(12) United States Patent
Zhang et al.

(10) Patent No.: US 12,292,426 B1
(45) Date of Patent: May 6, 2025

(54) METHOD FOR IDENTIFICATION OF CHARACTERISTIC COMPONENTS IN KAI-XIN-SAN BY THIN-LAYER CHROMATOGRAPHY (TLC)

(71) Applicant: Anhui University of Chinese Medicine, Hefei (CN)

(72) Inventors: Caiyun Zhang, Hefei (CN); Wenwen Tao, Hefei (CN); Xiaoxiao Shan, Hefei (CN); Dawei Li, Hefei (CN); Lele Zhou, Hefei (CN); Wenkang Tao, Hefei (CN); Hongyan Cheng, Hefei (CN)

(73) Assignee: Anhui University of Chinese Medicine, Hefei (CN)

( * ) Notice: Subject to any disclaimer, the term of this patent is extended or adjusted under 35 U.S.C. 154(b) by 0 days.

(21) Appl. No.: 19/012,222

(22) Filed: Jan. 7, 2025

(30) Foreign Application Priority Data

Aug. 15, 2024 (CN) .......................... 202411120819.1

(51) Int. Cl.
*G01N 30/94* (2006.01)
*G01N 33/15* (2006.01)

(52) U.S. Cl.
CPC ............. *G01N 30/94* (2013.01); *G01N 33/15* (2013.01)

(58) Field of Classification Search
CPC ................................ G01N 30/94; G01N 33/15

USPC ......................................................... 436/162
See application file for complete search history.

(56) References Cited

U.S. PATENT DOCUMENTS

2023/0181663 A1* 6/2023 Zhang ................. A61K 36/258
424/195.15

FOREIGN PATENT DOCUMENTS

| CN | 115267005 A | | 11/2022 | |
| CN | 115825272 A | * | 3/2023 | |
| WO | WO-2011113190 A1 | * | 9/2011 | ............. A61K 36/00 |

OTHER PUBLICATIONS

Wang, X. et al, Journal of Separation Science 2018, 41, 2672-2680. (Year: 2018).*

(Continued)

*Primary Examiner* — Arlen Soderquist
(74) *Attorney, Agent, or Firm* — WCF IP

(57) ABSTRACT

A method for identification of characteristic components in a Kai-Xin-San by thin-layer chromatography (TLC) is provided, belonging to the technical field of pharmaceutical raw material detection and traditional Chinese medicine quality control. The method only needs to prepare two test solutions to simultaneously identify six characteristic components in the Kai-Xin-San, namely ginsenoside Rb1, ginsenoside Re, tenuifolin, β-asarone, dehydrotumulosic acid, and pachymic acid. An automatic TLC spotting instrument can ensure even sampling and flat chromatographic bands and the silica gel G thin-layer plates after spotting are placed in the steam of the optimized developing solvent to allow pre-saturation.

8 Claims, 5 Drawing Sheets

(56) References Cited

OTHER PUBLICATIONS

Hu, Y. et al, Frontiers in Pharmacology 2020, 11, Article 561817, 8 pages with 1 page of supplementary material. (Year: 2020).*

BeiJi QianJin YaoFang (Essential Prescriptions Worth a Thousand in Gold for Every Emergency) Publishing Information: BeiJi QianJin YaoFang/ (Tang) Sun Simiao; Revised by Feng Wenquan—Taiyuan: Shanxi Science and Technology Press, Apr. 2020.

Pharmacopoeia of the People's Republic of China: 2020 Edition, 1/National Pharmacopoeia Commission, Beijing: China Medical Science and Technology Press, May 2020.

* cited by examiner

METHOD FOR IDENTIFICATION OF CHARACTERISTIC COMPONENTS IN KAI-XIN-SAN BY THIN-LAYER CHROMATOGRAPHY (TLC)

CROSS REFERENCE TO RELATED APPLICATION

This patent application claims the benefit and priority of Chinese Patent Application No. 202411120819.1 filed with the China National Intellectual Property Administration on Aug. 15, 2024, the disclosure of which is incorporated by reference herein in its entirety as part of the present application.

TECHNICAL FIELD

The present disclosure belongs to the technical field of pharmaceutical raw material detection and traditional Chinese medicine quality control, and particularly relates to a method for identification of characteristic components in a Kai-Xin-San by thin-layer chromatography (TLC).

BACKGROUND

The classic traditional Chinese medicine prescription Kai-Xin-San was first recited in "BeiJi QianJin YaoFang (Essential Prescriptions Worth a Thousand in Gold for Every Emergency)" by SUN Simiao in the Tang Dynasty. This prescription is composed of ginseng radix et rhizoma, polygalae radix, Poria, and Acori tatarinowii Rhizoma. This prescription has the effects of invigorating qi and nourishing the heart, as well as calming the mind and settling the spirit. Kai-Xin-San can be mainly used to treat symptoms such as deficiency of heart qi, restlessness, forgetfulness, and insomnia.

At present, main characteristic components in the Kai-Xin-San are identified by liquid chromatography (LC) and thin-layer chromatography (TLC). By LC, various components may be analyzed quantitatively when appropriate mobile phase and elution gradient were selected. For example, in Chinese patent Publication No. CN115267005A, a high-performance liquid chromatography (HPLC) was adopted to achieve quantitative analysis on five characteristic components in the Kai-Xin-San. However, the LC method requires extremely high equipment, technical level and professional knowledge in the operation process, as well as experimental conditions, and a long time for operation.

In comparison, TLC is an important experimental technique for rapid separation and qualitative analysis on small amounts of substances, with relatively simple equipment and operation procedures, as well as less sample dosage and duration. However, existing TLC processes are mainly for the analysis of a single herb in the Kai-Xin-San, while there is no detailed report on TLC identification for an entire prescription of the Kai-Xin-San. A general practice is to identify the four medicinal materials of ginseng radix et rhizoma, polygalae radix, Poria, and Acori tatarinowii Rhizoma separately according to TLC identification conditions corresponding to each of them in the Kai-Xin-San, which is difficult in meeting requirements for identification efficiency of the Kai-Xin-San during actual production. Moreover, due to complex ingredients of the prescription, the TLC of a single medicinal material cannot accurately eliminate interference. In the Kai-Xin-San, ginseng radix et rhizoma mainly includes active ingredients ginsenoside Rb1, ginsenoside Rg1, and ginsenoside Re; polygalae radix includes characteristic components such as tenuifolin; Poria includes characteristic components such as a triterpenoid compound pachymic acid and dehydrotumulosic acid; and Acori tatarinowii Rhizoma includes volatile oils (such as β-asarone). Due to their significant structural difference, the characteristic components are generally identified separately using specific identification methods and conditions in the prior art, greatly reducing an efficiency of the identification on the entire prescription of Kai-Xin-San. Accordingly, it is of great significance for identification of characteristic components and quality control of the Kai-Xin-San to achieve efficient identification of multiple characteristic components in the Kai-Xin-San under relatively simple analytical conditions by TLC.

SUMMARY

In view of the above problems, the present disclosure provides a TLC method for identification of characteristic components in a Kai-Xin-San by TLC, including the following steps:

collecting a first Kai-Xin-San test solution, a first Kai-Xin-San negative test solution, a first reference medicinal material solution, and a first standard solution, then spotting on a first silica gel G thin-layer plate to determine characteristic components in ginseng radix et rhizoma and polygalac radix;

collecting a second Kai-Xin-San test solution, a second Kai-Xin-San negative test solution, a second reference medicinal material solution, and a second standard solution, then spotting on a second silica gel G thin-layer plate to determine characteristic components in Poria and Acori tatarinowii Rhizoma;

developing the first silica gel G thin-layer plate with a developing solvent of dichloromethane (DCM)-n-butanol (n-BuOH)-water, developing the second silica gel G thin-layer plate with a developing solvent of DCM-ethyl acetate-formic acid, then taking out the first silica gel G thin-layer plate from the developing solvent and the second silica gel G thin-layer plate from the developing solvent to allow air-drying after the developing is completed; and spraying the first air-dried silica gel G thin-layer plate with a sulfuric acid-ethanol solution to allow color development inspection, and spraying the second air-dried silica gel G thin-layer plate with a vanillin sulfuric acid-ethanol mixed solution to allow color development inspection.

Further, the characteristic components in the ginseng radix et rhizoma and the polygalae radix include ginsenoside Rb1, ginsenoside Re, and tenuifolin; and the characteristic components in the Poria and the Acori tatarinowii Rhizoma include-asarone, dehydrotumulosic acid, and pachymic acid.

Further, the first Kai-Xin-San test solution is prepared by subjecting Kai-Xin-San to ultrasonic dissolution in 80% to 95% ethanol at a mass-to-volume ratio of 1 g: 10 mL;

the first Kai-Xin-San negative test solution is an Acori tatarinowii Rhizoma-Poria solution prepared by subjecting the Acori tatarinowii Rhizoma and the Poria to ultrasonic dissolution in the 80% to 95% ethanol at a mass-to-volume ratio of 1.5 g: 25 mL; where the Acori tatarinowii Rhizoma and the Acori tatarinowii Rhizoma-Poria solution are at a mass-to-volume ratio of 0.5 g: 25 mL, and the Poria and the Acori tatarinowii Rhizoma-Poria solution are at a mass-to-volume ratio of 1 g: 25 mL;

the first reference medicinal material solution includes a polygalae radix reference medicinal material solution prepared by subjecting the polygalae radix to ultrasonic dissolution in the 80% to 95% ethanol at a mass-to-volume ratio of 1 g: 50 mL and a ginseng radix et rhizoma reference medicinal material solution prepared by subjecting the ginseng radix et rhizoma to ultrasonic dissolution in the 80% to 95% ethanol at a mass-to-volume ratio of 1 g: 50 mL; and the first standard solution includes a ginsenoside Rb1 standard solution prepared by dissolving ginsenoside Rb1 in methanol at a mass-to-volume ratio of 1 mg: 1 mL, a ginsenoside Re standard solution prepared by dissolving ginsenoside Re in the methanol at a mass-to-volume ratio of 1 mg: 1 mL, and a tenuifolin standard solution prepared by dissolving tenuifolin in the methanol at a mass-to-volume ratio of 1 mg: 1 mL.

Further, the second Kai-Xin-San test solution is prepared by subjecting Kai-Xin-San to ultrasonic dissolution in DCM at a mass-to-volume ratio of 1 g: 10 mL;

the second Kai-Xin-San negative test solution is a ginseng radix et rhizoma-polygalae radix solution prepared by subjecting the ginseng radix et rhizoma and the polygalae radix to ultrasonic dissolution in the DCM at a mass-to-volume ratio of 1 g: 25 mL; where the ginseng radix et rhizoma and the ginseng radix et rhizoma-polygalae radix solution are at a mass-to-volume ratio of 0.5 g: 25 mL, and the polygalae radix and the ginseng radix et rhizoma-polygalae radix solution are at a mass-to-volume ratio of 0.5 g: 25 mL;

the second reference medicinal material solution includes an Acori tatarinowii Rhizoma reference medicinal material solution prepared by subjecting the Acori tatarinowii Rhizoma to ultrasonic dissolution in the DCM at a mass-to-volume ratio 1 g: 50 mL and a Poria reference medicinal material solution prepared by subjecting the Poria to ultrasonic dissolution in the DCM at a mass-to-volume ratio of 1 g: 25 mL; and the second reference substance solution includes a β-asarone reference substance solution prepared by dissolving β-asarone in methanol at a mass-to-volume ratio of 1 mg: 1 mL, a dehydrotumulosic acid reference substance solution prepared by dissolving dehydrotumulosic acid in the methanol at a mass-to-volume ratio of 1 mg: 1 mL, and a pachymic acid reference substance solution prepared by dissolving pachymic acid in the methanol at a mass-to-volume ratio of 1 mg: 1 mL.

Further, the first Kai-Xin-San test solution, the first Kai-Xin-San negative test solution, the first reference medicinal material solution, and the first reference substance solution are spotted at a volume ratio of 15:15:8:6; and the second Kai-Xin-San test solution, the second Kai-Xin-San negative test solution, the second reference medicinal material solution, and the second reference substance solution are spotted at a volume ratio of 15:15: 8:6.

Further, DCM, n-BuOH, and water in the developing solvent of DCM-n-BuOH-water are at a volume ratio of (7-8): 4:1, preferably 7:8:1.

Further, DCM, ethyl acetate, and formic acid in the developing solvent of DCM-ethyl acetate-formic acid are at a volume ratio of 12:3:(0.25-0.5), preferably 12:3:0.5.

Further, the sulfuric acid-ethanol mixed solution has a mass percentage concentration of 5%, and a sulfuric acid solution and an ethanol solution are at a volume ratio of 1:19.

Further, the vanillin sulfuric acid-ethanol mixed solution has a mass percentage concentration of 2%, and a vanillin sulfuric acid solution and an ethanol solution are at a volume ratio of 1:9.

Further, the color development inspection is conducted under sunlight or a 365 nm ultraviolet lamp.

The present disclosure has the following beneficial effects:

The method only needs to prepare two test solutions by solution ultrasonic extraction to simultaneously identify six characteristic components in the Kai-Xin-San effectively, namely ginsenoside Rb1, ginsenoside Re, tenuifolin, β-asarone, dehydrotumulosic acid, and pachymic acid. Spotting with an automatic spotter can ensure that spotting is even and level, and the silica gel G thin-layer plates after spotting are placed in the steam of a developing solvent to allow pre-saturation, which also can ensure that spotting is even and level. Moreover, bands are flat during developing, which improves an accuracy of the identification. Moreover, negative test solutions and reference medicinal material solutions set in the TLC can achieve clearer chromatographic comparison. The experimental results show that the method has desirable applicability, clear chromatograms, and excellent separation, which can significantly improve a success rate for the TLC identification of Kai-Xin-San and meets the requirements for identification efficiency of Kai-Xin-San in actual production. At the same time, the TLC characteristic components of Poria and Acori tatarinowii Rhizoma in the 2020 edition of the "Chinese Pharmacopoeia" are identified in the present disclosure, which is of great significance for the establishment of quality control characteristics for Poria and Acori tatarinowii Rhizoma medicinal materials.

Other features and advantages of the present disclosure will be illustrated in the following description, and some of these will become apparent from the description or be understood by implementing the present disclosure. The objectives and other advantages of the present disclosure can be implemented or obtained by structures specifically indicated in the description, claims, and accompanying drawings.

BRIEF DESCRIPTION OF THE DRAWINGS

To describe the technical solutions in the embodiments of the present disclosure or in the prior art more clearly, the following briefly describes the accompanying drawings required for describing the embodiments or the prior art. Apparently, the accompanying drawings in the following description show merely some embodiments of the present disclosure, and those skilled in the art may still derive other drawings from these accompanying drawings without creative efforts.

DETAILED DESCRIPTION OF THE EMBODIMENTS

Figure 1:
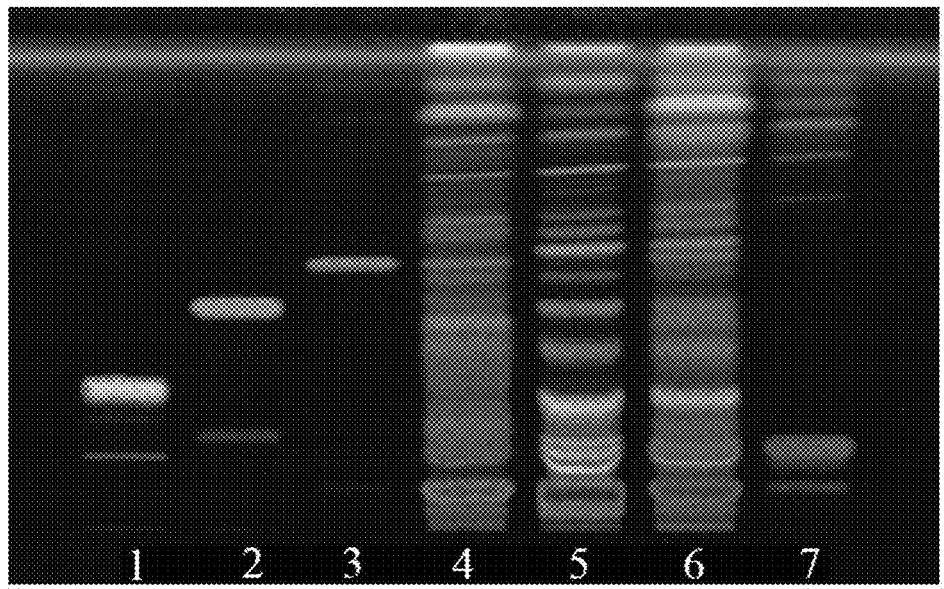
FIG. 1 shows a TLC analysis of ginsenoside Rb1, ginsenoside Re, and tenuifolin in the Kai-Xin-San in Example 1.

In order to make the objectives, technical solutions, and advantages of the examples of the present disclosure clearer, the technical solutions in the examples of the present disclosure will be clearly and completely described below in conjunction with the drawings of the examples of the present disclosure. Apparently, the described examples are merely some of, rather than all of the examples of the present disclosure. All other examples obtained by those skilled in the art based on the examples of the present disclosure without creative efforts shall fall within the protection scope of the present disclosure.

Example 1

A method for identification of ginsenoside Rb1 and ginsenoside Re in ginseng radix et rhizoma and tenuifolin in polygalae radix in a Kai-Xin-San by TLC, including the following steps:

Preparation of a first Kai-Xin-San test solution: 2.5 g of the Kai-Xin-San powder was added into 25 mL of 90% ethanol and a resulting liquid was subjected to ultrasonic treatment (power 250 W, frequency 50 kHz) for 45 min, a resulting product was filtered, a resulting filtrate was evaporated to dryness, and a resulting residue was dissolved into 1 mL of methanol to obtain the first Kai-Xin-San test solution.

Preparation of a first Kai-Xin-San negative test solution: 0.5 g of an Acori tatarinowii Rhizoma powder and 1 g of a Poria powder were added into 25 mL of 90% ethanol and subjected to ultrasonic treatment (power 250 W, frequency 50 kHz) for 45 min, a product was filtered, a filtrate was evaporated to dryness, and a residue was dissolved in 1 mL of methanol to obtain the first Kai-Xin-San negative test solution.

Preparation of a first reference medicinal material solution: 0.5 g of a polygalae radix reference medicinal material and 0.5 g of a ginseng radix et rhizoma reference medicinal material were prepared according to the preparation method of the first Kai-Xin-San test solution to obtain a polygalae radix reference medicinal material solution and a ginseng ginseng radix et rhizoma reference medicinal material solution.

Preparation of a first standard solution: a ginsenoside Rb1 standard, a ginsenoside Re standard, and a tenuifolin standard were dissolved in methanol separately to obtain 1 mL of a standard solution containing 1 mg of the standard, namely a ginsenoside Rb1 standard solution, a ginsenoside Re standard solution, and a tenuifolin standard solution.

Spotting: according to the TLC test (Chinese Pharmacopocia 2020 Edition Part IV General Rules 0502), 15 μL of the first Kai-Xin-San test solution, 15 μL of the first Kai-Xin-San negative test solution, 8 μL of the first reference medicinal material solution (8 μL each of the polygalae radix reference medicinal material solution and the ginseng radix et rhizoma reference medicinal material solution), and 6 μL of the first standard solution (6 μL each of the ginsenoside Rb1 standard solution, the ginsenoside Re standard solution, and the tenuifolin standard solution), and spotted on a first silica gel G thin-layer plate; an automatic spotter was used during the spotting to ensure that the spotting was even and level.

Developing: a mixed solution of DCM-n-BuOH-water with a volume ratio of 7:4:1 was used as a developing solvent, the spotted first silica gel G thin-layer plate was placed in vapor of the developing solvent to allow pre-saturation, then developed, taken out, and dried.

Inspection: a 5% sulfuric acid-ethanol solution (a volume ratio of sulfuric acid solution to ethanol solution was 1:19) was sprayed on the air-dried first silica gel G thin-layer plate, heated at 105° C. until spots were clearly color-developed, then inspected under UV lamp (365 nm).

The results were shown in FIG. 1, where 1 represented the ginsenoside Rb1 standard solution; 2 represented the ginsenoside Re standard solution; 3 represented the tenuifolin standard solution; 4 represented the polygalae radix reference medicinal material solution; 5 represented the ginseng radix et rhizoma reference medicinal material solution; 6 represented the first Kai-Xin-San test solution; and 7 represented the first Kai-Xin-San negative test solution. The results showed that in the chromatogram of the Kai-Xin-San negative test solution, a main spot of the same color appeared at the corresponding position in the chromatogram of the reference medicinal material.

Example 2

This example provided a method for identification of β-asarone and dehydrotumulosic acid in Acori tatarinowii Rhizoma and pachymic acid in Poria in a Kai-Xin-San by TLC, including the following steps:

Preparation of a second Kai-Xin-San test solution: 2.5 g of the Kai-Xin-San was added with 25 mL of DCM and subjected to ultrasonic treatment (power 250 W, frequency 50 kHz) for 20 min, a product was filtered, a filtrate was evaporated to dryness, and a residue was dissolved in 1 mL of methanol to obtain the second Kai-Xin-San test solution.

Preparation of a second Kai-Xin-San negative test solution: 0.5 g of a ginseng radix et rhizoma powder and 0.5 g of a polygalae radix powder were added with 25 mL of DCM and subjected to ultrasonic treatment (power 250 W, frequency 50 kHz) for 20 min, a product was filtered, a filtrate was evaporated to dryness, and a residue was dissolved in 1 mL of methanol to obtain the second Kai-Xin-San negative test solution.

Preparation of a second reference medicinal material solution: 0.5 g of an Acori tatarinowii Rhizoma reference medicinal material and 1 g of a Poria reference medicinal material were prepared according to the preparation method of the second Kai-Xin-San test solution to obtain a Poria reference medicinal material solution and an Acori tatarinowii Rhizoma reference medicinal material solution.

Preparation of a second standard solution: a β-asarone standard, a dehydrotumulosic acid standard, and a pachymic acid standard were dissolved in methanol separately to obtain 1 mL of a solution containing 1 mg of the standard, namely a β-asarone standard solution, a dehydrotumulosic acid standard solution, and a pachymic acid standard solution.

Spotting: according to the TLC test (Chinese Pharmacopocia 2020 Edition Part IV General Rules 0502), 15 μL of the second Kai-Xin-San test solution, 15 μL of the second Kai-Xin-San negative test solution, 8 μL of the second reference medicinal material solution (8 μL each of the Poria reference medicinal material solution and the Acori tatarinowii Rhizoma reference medicinal material solution), and 6 μL of the second standard solution (6 μL each of the β-asarone standard solution, the dehydrotumulosic acid standard solution, and the pachymic acid standard solution), and spotted on a second silica gel G thin-layer plate; an automatic spotter was used during the spotting to ensure that the spotting was even and level.

Developing: a mixed solution of DCM-ethyl acetate-formic acid with a volume ratio of 12:3:0.5 was used as a developing solvent, the spotted second silica gel G thin-layer plate was placed in vapor of the developing solvent to allow pre-saturation, then developed, taken out, and dried.

Inspection: a 2% vanillin sulfuric acid-ethanol mixed solution (a volume ratio of vanillin sulfuric acid solution to ethanol solution was 1:9) was sprayed on the air-dried second silica gel G thin-layer plate, heated at 105° C. until spots were clearly color-developed.

Figure 2:
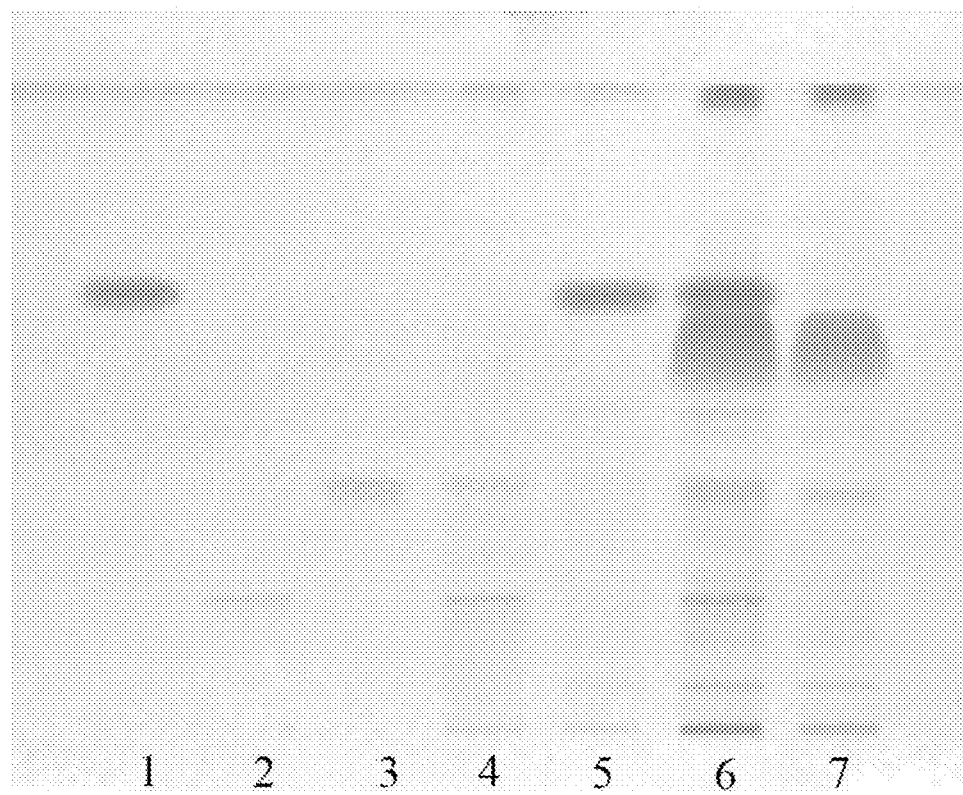
FIG. 2 shows a TLC analysis of β-asarone, dehydrotumulosic acid, and pachymic acid in the Kai-Xin-San in Example 2.

The results were shown in FIG. 2, where 1 represented the β-asarone standard solution; 2 represented the dehydrotumulosic acid standard solution; 3 represented the pachymic acid standard solution; 4 represented the Poria reference medicinal material solution; 5 represented the Acori tatarinowii Rhizoma reference medicinal material solution; 6 represented the second Kai-Xin-San test solution; and 7 represented the second Kai-Xin-San negative test solution. The results showed that in the chromatogram of the Kai-Xin-San negative test solution, a main spot of the same color appeared at the corresponding position in the chromatogram of the reference medicinal material, showing desirable separation effect.

Example 1-1

The characteristic components in polygalae radix and ginseng radix et rhizoma in Kai-Xin-San were identified by TLC in a same manner as that in Example 1, except that 90% ethanol was replaced by 80% ethanol for ultrasonic extraction during the preparation.

The results showed that in the chromatogram of the Kai-Xin-San negative test solution, a main spot of the same color appeared at the corresponding position in the chromatogram of the reference medicinal material; the spot was slightly blurred compared to 90% ethanol but was still discernible.

Example 1-2

The characteristic components in polygalae radix and ginseng radix et rhizoma in Kai-Xin-San were identified by TLC in a same manner as that in Example 1, except that 90% ethanol was replaced by 95% ethanol for ultrasonic extraction during the preparation.

The results showed that in the chromatogram of the Kai-Xin-San negative test solution, a main spot of the same color appeared at the corresponding position in the chromatogram of the reference medicinal material.

Comparative Example 1-1

The characteristic components in polygalae radix and ginseng radix et rhizoma in Kai-Xin-San were identified by TLC in a same manner as that in Example 1, except that 90% ethanol was replaced by 70% ethanol for ultrasonic extraction during the preparation.

Figure 3:
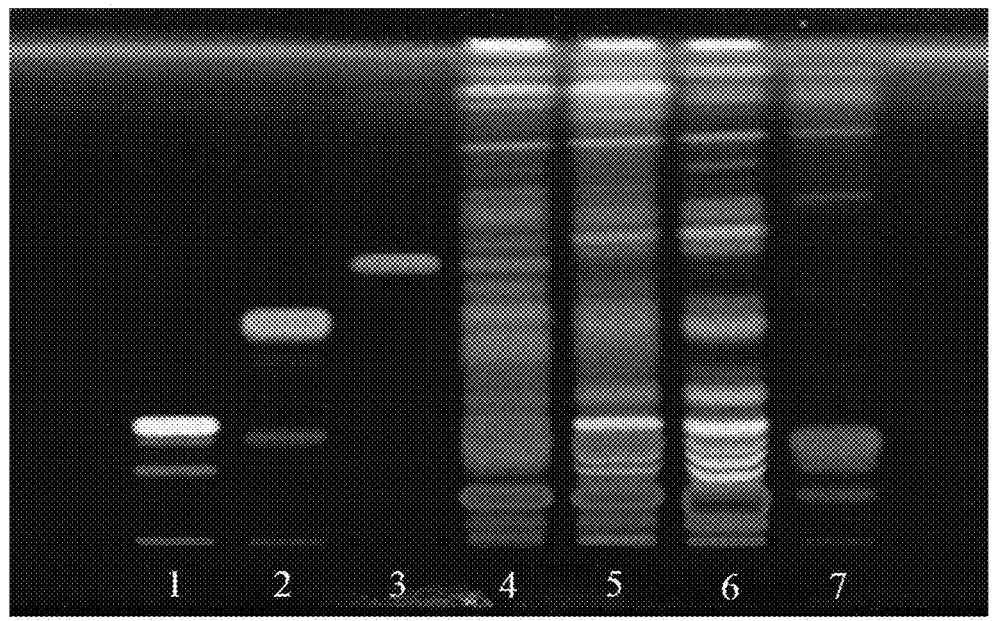
FIG. 3 shows a TLC analysis of ginsenoside Rb1, ginsenoside Re, and tenuifolin in the Kai-Xin-San in Comparative Example 1-1.

The results were shown in FIG. 3, where 1 represented the ginsenoside Rb1 standard solution; 2 represented the ginsenoside Re standard solution; 3 represented the tenuifolin standard solution; 4 represented the polygalae radix reference medicinal material solution; 5 represented the ginseng radix et rhizoma reference medicinal material solution; 6 represented the first Kai-Xin-San test solution; and 7 represented the first Kai-Xin-San negative test solution. The results showed that there was a poor development effect. The main color spot at the position corresponding to the chromatogram of the reference medicinal material was blurred, and the spot was blurred compared with the 90% ethanol ultrasonic extraction.

Comparative Example 1-2

The characteristic components in polygalae radix and ginseng radix et rhizoma in Kai-Xin-San were identified by TLC in a same manner as that in Example 1, except that the developing solvent in the developing was a mixed solution of DCM-n-BuOH-water at a volume ratio of 9:4:1.

Figure 4:
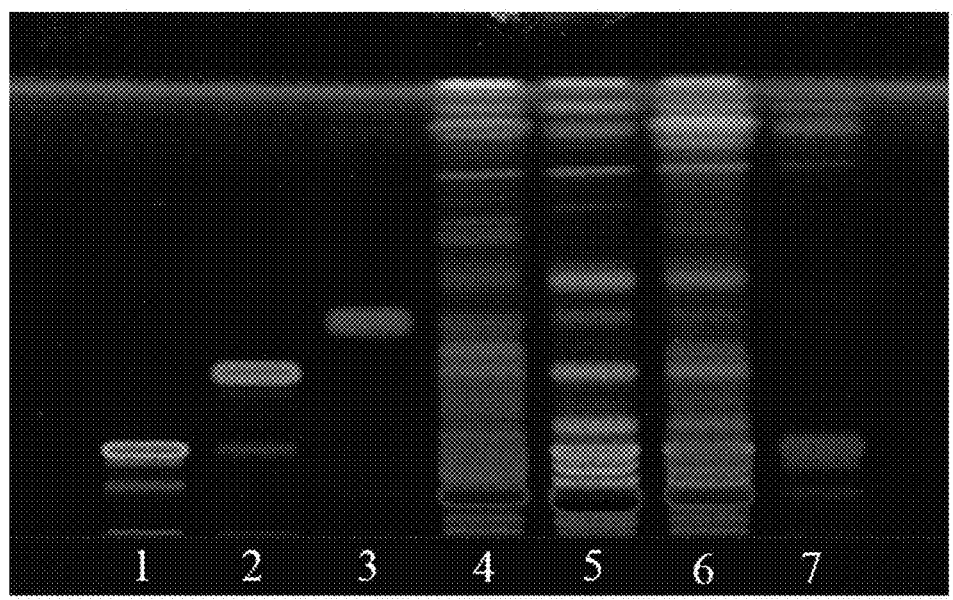
FIG. 4 shows a TLC analysis of ginsenoside Rb1, ginsenoside Re, and tenuifolin in the Kai-Xin-San in Comparative Example 1-2.

The results were shown in FIG. 4, where 1 represented the ginsenoside Rb1 standard solution; 2 represented the ginsenoside Re standard solution; 3 represented the tenuifolin standard solution; 4 represented the polygalae radix reference medicinal material solution; 5 represented the ginseng radix et rhizoma reference medicinal material solution; 6 represented the first Kai-Xin-San test solution; and 7 represented the first Kai-Xin-San negative test solution. The results showed that there was a poor development effect. The main colored spot at the position corresponding to the chromatogram of the reference medicinal material was blurred, and the ginseng radix et rhizoma reference medicinal material interfered with the color development of the tenuifolin spot.

Comparative Example 1-3

The characteristic components in polygalae radix and ginseng radix et rhizoma in Kai-Xin-San were identified by TLC in a same manner as that in Example 1, except that the developing solvent in the developing was a mixed solution of DCM-n-BuOH-water at a volume ratio of 13:7:2.

Figure 5:
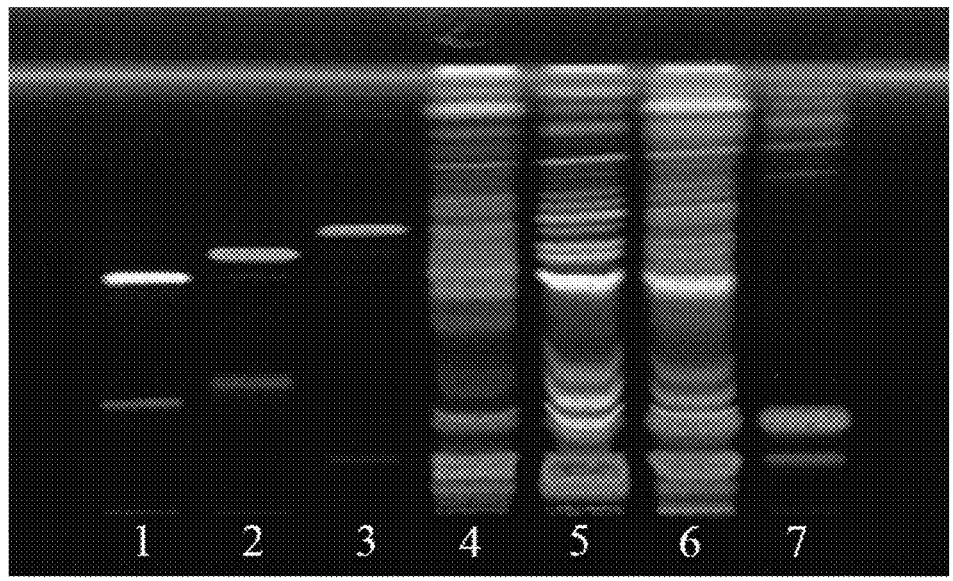
FIG. 5 shows a TLC analysis of ginsenoside Rb1, ginsenoside Re, and tenuifolin in the Kai-Xin-San in Comparative Example 1-3.

The results were shown in FIG. 5, where 1 represented the ginsenoside Rb1 standard solution; 2 represented the ginsenoside Re standard solution; 3 represented the tenuifolin standard solution; 4 represented the polygalae radix reference medicinal material solution; 5 represented the ginseng radix et rhizoma reference medicinal material solution; 6 represented the first Kai-Xin-San test solution; and 7 represented the first Kai-Xin-San negative test solution. The results showed that there was a poor development effect. The main colored spot at the position corresponding to the chromatogram of the reference medicinal material was rather fuzzy; and compared with the developing solvent DCM-n-BuOH-water (at a volume ratio of 7:4:1), the tenuifolin spot in the Kai-Xin-San test solution was not obvious.

Comparative Example 1-4

The characteristic components in polygalae radix and ginseng radix et rhizoma in Kai-Xin-San were identified by TLC in a same manner as that in Example 1, except that the first standard solution was spotted at 8 µL during the spotting.

Figure 6:
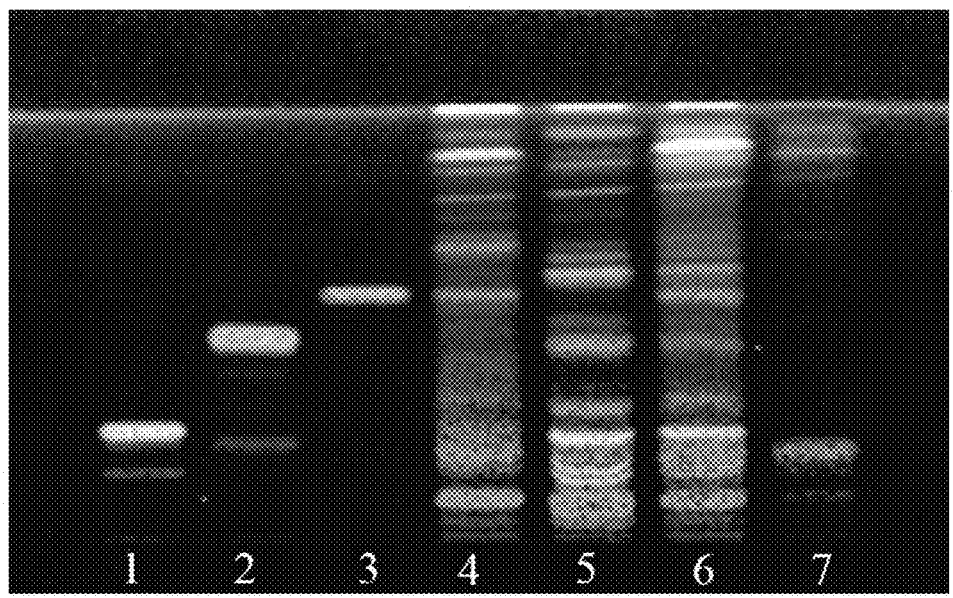
FIG. 6 shows a TLC analysis of ginsenoside Rb1, ginsenoside Re, and tenuifolin in the Kai-Xin-San in Comparative Example 1-4.

The results were shown in FIG. 6, where 1 represented the ginsenoside Rb1 standard solution; 2 represented the ginsenoside Re standard solution; 3 represented the tenuifolin standard solution; 4 represented the polygalae radix reference medicinal material solution; 5 represented the ginseng radix et rhizoma reference medicinal material solution; 6 represented the first Kai-Xin-San test solution; and 7 represented the first Kai-Xin-San negative test solution. The results showed that there was a poor development effect. The main colored spot at the position corresponding to the chromatogram of the reference medicinal material was fuzzy, and the spots of a same color were not clear.

In addition, results when the standard solution was spotted at 4 µL were also explored.

The results showed that the main spot of the same color appeared at the position corresponding to the chromatogram of the reference medicinal material, but the tenuifolin spot was lighter in color.

Example 2-1

The characteristic components in Acori tatarinowii Rhizoma and Poria in Kai-Xin-San were identified by TLC in a same manner as that in Example 2, except that the developing solvent in the developing was a mixed solution of DCM-ethyl acetate-formic acid at a volume ratio of 12:3:0.25.

Figure 7:
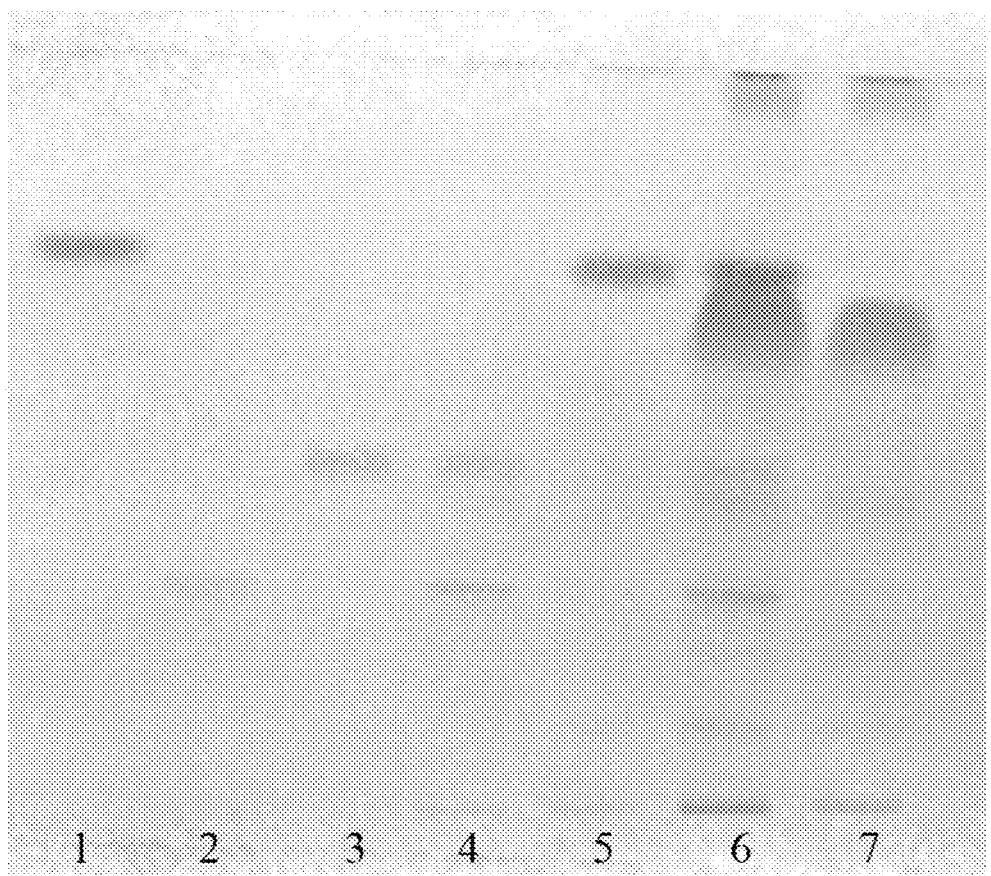
FIG. 7 shows a TLC analysis of β-asarone, dehydrotumulosic acid, and pachymic acid in the Kai-Xin-San in Example 2-1.

The results were shown in FIG. 7, where 1 represented the β-asarone standard solution; 2 represented the dehydrotumulosic acid standard solution; 3 represented the pachymic acid standard solution; 4 represented the Poria reference medicinal material solution; 5 represented the Acori tatarinowii Rhizoma reference medicinal material solution; 6 represented the second Kai-Xin-San test solution; and 7 represented the second Kai-Xin-San negative test solution. The results showed that a main spot of the same color appeared at the corresponding position in the chromatogram of the reference medicinal material, and the spot had clear color development, showing desirable separation effect.

Comparative Example 2-1

The characteristic components in Acori tatarinowii Rhizoma and Poria in Kai-Xin-San were identified by TLC in a same manner as that in Example 2, except that the developing solvent in the developing was a mixed solution of DCM-ethyl acetate-formic acid at a volume ratio of 20:5:0.25.

Figure 8:
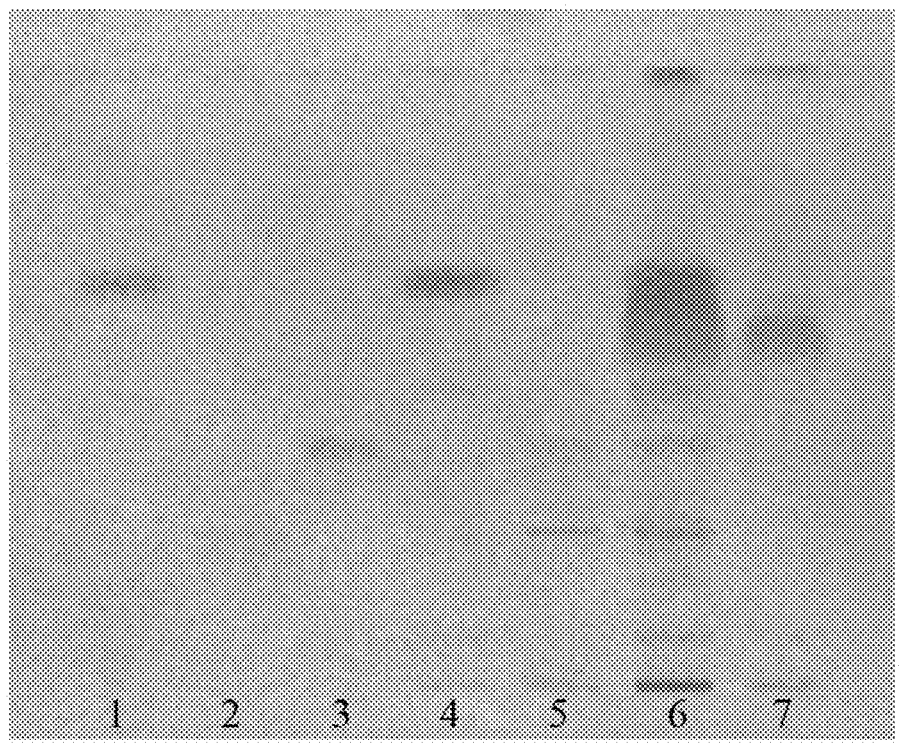
FIG. 8 shows a TLC analysis of β-asarone, dehydrotumulosic acid, and pachymic acid in the Kai-Xin-San in Comparative Example 2-1.

The results were shown in FIG. 8, where 1 represented the β-asarone standard solution; 2 represented the dehydrotumulosic acid standard solution; 3 represented the pachymic acid standard solution; 4 represented the Poria reference medicinal material solution; 5 represented the Acori tatarinowii Rhizoma reference medicinal material solution; 6 represented the second Kai-Xin-San test solution; and 7 represented the second Kai-Xin-San negative test solution. The results showed that a main spot of the same color appeared at the corresponding position on the chromatogram of the reference medicinal material, but there was a poor separation effect of β-asarone in the entire prescription.

Comparative Example 2-2

The characteristic components in Acori tatarinowii Rhizoma and Poria in Kai-Xin-San were identified by TLC in a same manner as that in Example 2, except that the developing solvent in the developing was a mixed solution of chloroform-ethyl acetate-formic acid at a volume ratio of 12:3:0.5.

Figure 9:
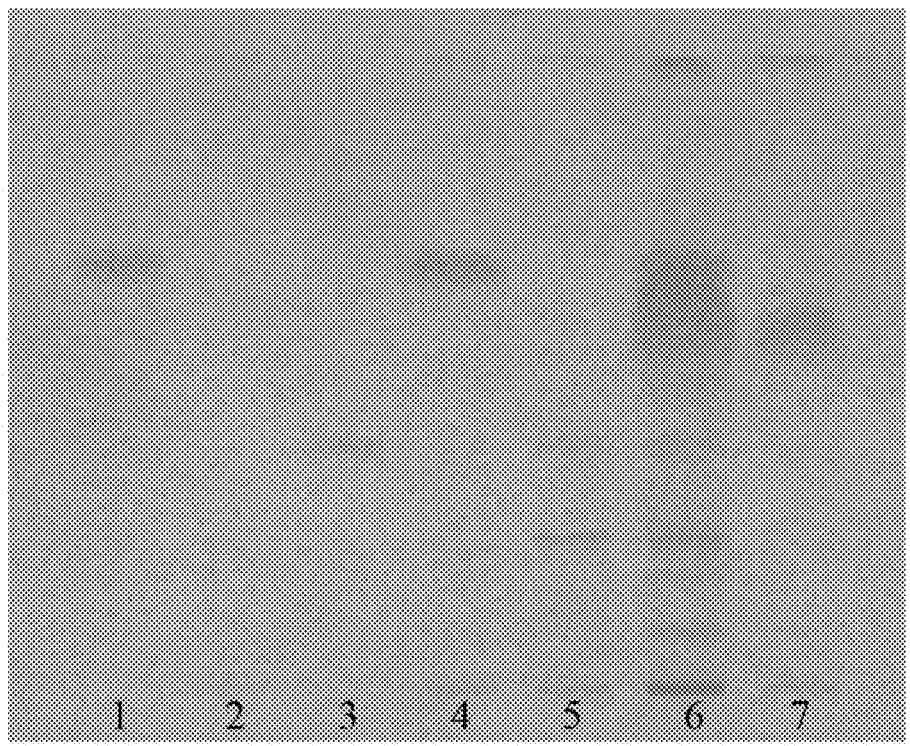
FIG. 9 shows a TLC analysis of β-asarone, dehydrotumulosic acid, and pachymic acid in the Kai-Xin-San in Comparative Example 2-2.

The results were shown in FIG. 9, where 1 represented the β-asarone standard solution; 2 represented the dehydrotumulosic acid standard solution; 3 represented the pachymic acid standard solution; 4 represented the Poria reference medicinal material solution; 5 represented the Acori tatarinowii Rhizoma reference medicinal material solution; 6 represented the second Kai-Xin-San test solution; and 7 represented the second Kai-Xin-San negative test solution. The results showed that a main spot of the same color appeared at the corresponding position in the chromatogram of the reference medicinal material. However, spot of dehydrotumulosic acid standard solution was not clear, and there was still a poor separation effect of β-asarone in the entire prescription.

Comparative Example 2-3

The characteristic components in Acori tatarinowii Rhizoma and Poria in Kai-Xin-San were identified by TLC in a same manner as that in Example 2, except that the second standard solution was spotted at 4 µL during the spotting.

Figure 10:
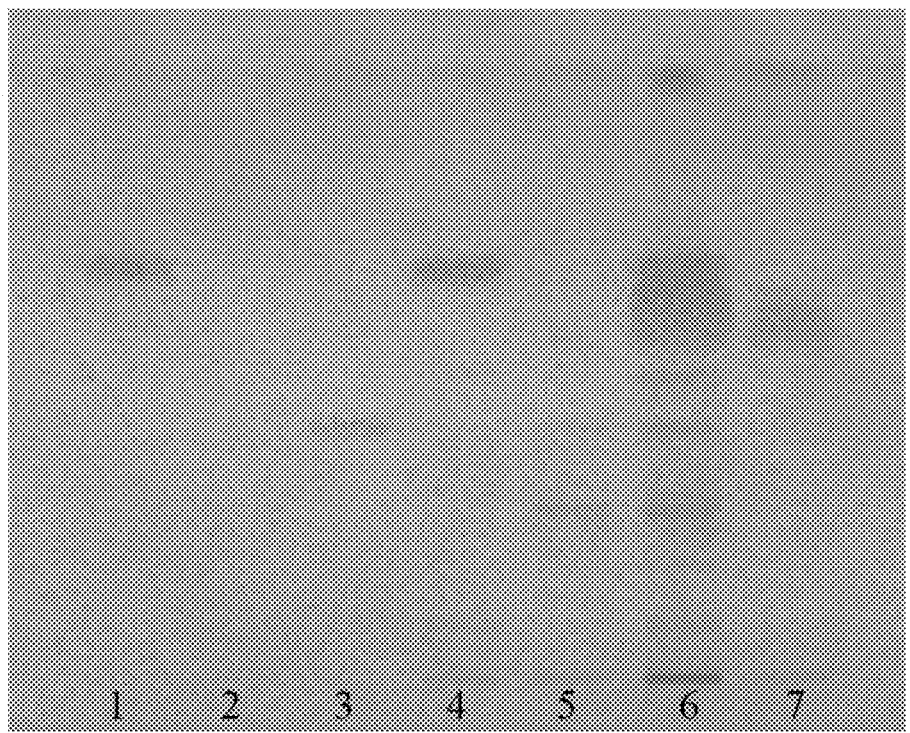
FIG. 10 shows a TLC analysis of β-asarone, dehydrotumulosic acid, and pachymic acid in the Kai-Xin-San in Comparative Example 2-3.

The results were shown in FIG. 10, where 1 represented the β-asarone standard solution; 2 represented the dehydrotumulosic acid standard solution; 3 represented the pachymic acid standard solution; 4 represented the Poria reference medicinal material solution; 5 represented the Acori tatarinowii Rhizoma reference medicinal material solution; 6 represented the second Kai-Xin-San test solution; and 7 represented the second Kai-Xin-San negative test solution. The results showed that a main spot of the same color appeared at the corresponding position in the chromatogram of the reference medicinal material. However, spot of dehydrotumulosic acid standard solution was slightly light.

Although the present disclosure is described in detail with reference to the foregoing examples, those of ordinary skill in the art should understand that they can still modify the technical solutions described in the foregoing examples, or make equivalent substitutions on some technical features therein. These modifications or substitutions do not make the essence of the corresponding technical solutions deviate from the spirit and scope of the technical solutions of the examples of the present disclosure.

What is claimed is:

1. A method for identification of characteristic components in a Kai-Xin-San by thin-layer chromatography (TLC), comprising the following steps:
    collecting a first test solution of Kai-Xin-San, a first negative test solution of Kai-Xin-San, a first reference medicinal material solution, and a first standard solution, then spotting on a first silica gel G thin-layer plate to determine characteristic components in ginseng radix et rhizoma and polygalae radix, respectively;
    collecting a second test solution of Kai-Xin-San, a second negative test solution of Kai-Xin-San, a second reference medicinal material solution, and a second standard solution, then spotting on a second silica gel G thin-layer plate to determine characteristic components in Poria and Acori tatarinowii Rhizoma, respectively;

developing the first silica gel G thin-layer plate with a developing solvent of dichloromethane (DCM)-n-butanol (n-BuOH)-water, developing the second silica gel G thin-layer plate with a developing solvent of DCM-ethyl acetate-formic acid, then taking out the first silica gel G thin-layer plate from the developing solvent and the second silica gel G thin-layer plate from the developing solvent to allow air-drying after the developing is completed; wherein DCM, n-BuOH, and water in the developing solvent of DCM-n-BuOH-water are at a volume ratio of 7-8:4:1, and DCM, ethyl acetate, and formic acid in the developing solvent of DCM-ethyl acetate-formic acid are at a volume ratio of 12:3:0.25-0.5; and spraying the first air-dried silica gel G thin-layer plate with a sulfuric acid-ethanol solution for color development inspection, and spraying the second air-dried silica gel G thin-layer plate with a vanillin sulfuric acid-ethanol mixed solution for color development inspection.

2. The method for identification of characteristic components in a Kai-Xin-San by TLC according to claim 1, wherein the characteristic components in the ginseng radix et rhizoma and the polygalae radix comprise ginsenoside Rb1, ginsenoside Re, and tenuifolin; and the characteristic components in the Poria and the Acori tatarinowii Rhizoma comprise β-asarone, dehydrotumulosic acid, and pachymic acid.

3. The method for identification of characteristic components in a Kai-Xin-San by TLC according to claim 1, wherein the first test solution of Kai-Xin-San is prepared by subjecting the Kai-Xin-San to ultrasonic dissolution in 80% to 95% ethanol at a mass-to-volume ratio of 1 g: 10 mL;

the first negative test solution of Kai-Xin-San is an Acori tatarinowii Rhizoma-Poria solution prepared by subjecting the Acori tatarinowii Rhizoma and the Poria to ultrasonic dissolution in the 80% to 95% ethanol at a mass-to-volume ratio of 1.5 g: 25 mL; wherein, the Acori tatarinowii Rhizoma and the Poria in the first negative test solution of Kai-Xin-San are at a mass-to-volume ratio of 0.5 g: 25 mL, and 1 g: 25 mL, respectively;

the first reference medicinal material solution comprises a polygalae radix reference medicinal material solution prepared by subjecting the polygalae radix to ultrasonic dissolution in the 80% to 95% ethanol at a mass-to-volume ratio of 1 g: 50 mL and a ginseng radix ct rhizoma reference medicinal material solution prepared by subjecting the ginseng radix ct rhizoma to ultrasonic dissolution in the 80% to 95% ethanol at a mass-to-volume ratio of 1 g: 50 mL; and the first standard solution comprises a ginsenoside Rb1 standard solution prepared by dissolving ginsenoside Rb1 in methanol at a mass-to-volume ratio of 1 mg: 1 mL, a ginsenoside Re standard solution prepared by dissolving ginsenoside Re in methanol at a mass-to-volume ratio of 1 mg: 1 mL, and a tenuifolin standard solution prepared by dissolving tenuifolin in methanol at a mass-to-volume ratio of 1 mg: 1 mL, respectively.

4. The method for identification of characteristic components in a Kai-Xin-San by TLC according to claim 1, wherein the second test solution of Kai-Xin-San is prepared by subjecting Kai-Xin-San to ultrasonic dissolution in DCM at a mass-to-volume ratio of 1 g: 10 mL;

the second negative test solution of Kai-Xin-San is a ginseng radix et rhizoma-polygalac radix solution prepared by subjecting the ginseng radix et rhizoma and the polygalae radix to ultrasonic dissolution in the DCM at a mass-to-volume ratio of 1 g: 25 mL; wherein the ginseng radix et rhizoma and the ginseng radix et rhizoma-polygalae radix solution are at a mass-to-volume ratio of 0.5 g: 25 mL, and the polygalae radix and the ginseng radix et rhizoma-polygalae radix solution are at a mass-to-volume ratio of 0.5 g: 25 mL, respectively; the second reference medicinal material solution comprises an Acori tatarinowii Rhizoma reference medicinal material solution prepared by subjecting the Acori tatarinowii Rhizoma to ultrasonic dissolution in the DCM at a mass-to-volume ratio 1 g: 50 mL and a Poria reference medicinal material solution prepared by subjecting the Poria to ultrasonic dissolution in the DCM at a mass-to-volume ratio of 1 g: 25 mL, respectively; and the second standard solution comprises a β-asarone standard solution prepared by dissolving three standards of β-asarone, dehydrotumulosic acid, and pachymic acid in methanol at a mass-to-volume ratio of 1 mg: 1 mL, respectively.

5. The method for identification of characteristic components in a Kai-Xin-San by TLC according to claim 1, wherein the spotting volumes of the first Kai-Xin-San test solution, the first Kai-Xin-San negative test solution, the first reference medicinal material solution, and the first standard solution are at a volume ratio of 15:15:8:6; and the spotting volumes of the second Kai-Xin-San test solution, the second Kai-Xin-San negative test solution, the second reference medicinal material solution, and the second standard solution are at a volume ratio of 15:15:8:6.

6. The method for identification of characteristic components in a Kai-Xin-San by TLC according to claim 1, wherein a mass percentage concentration in the sulfuric acid-ethanol solution is 5%, and a volume ratio of sulfuric acid solution to ethanol solution is 1:19.

7. The method for identification of characteristic components in a Kai-Xin-San by TLC according to claim 1, wherein a mass percentage concentration of vanillin sulfuric acid-ethanol mixed solution is 2%, and a volume ratio of a vanillin sulfuric acid solution to an ethanol solution is 1:9.

8. The method for identification of characteristic components in a Kai-Xin-San by TLC according to claim 1, wherein the color development inspection is conducted under sunlight or a 365 nm ultraviolet lamp.

* * * * *